(12) United States Patent
Shdaimah et al.

(10) Patent No.: US 7,635,092 B2
(45) Date of Patent: *Dec. 22, 2009

(54) HUMIDITY-CONTROLLED CHAMBER FOR A THERMOGRAVIMETRIC INSTRUMENT

(75) Inventors: Amichai Shdaimah, Ardmore, PA (US); John R. Reader, Jr., Newark, DE (US); Eric Pilacik, East Norriton, PA (US)

(73) Assignee: Waters Technologies Corporation, Milford, MA (US)

( * ) Notice: Subject to any disclaimer, the term of this patent is extended or adjusted under 35 U.S.C. 154(b) by 760 days.

This patent is subject to a terminal disclaimer.

(21) Appl. No.: 11/349,338

(22) Filed: Feb. 8, 2006

(65) Prior Publication Data

US 2006/0208098 A1    Sep. 21, 2006

Related U.S. Application Data

(63) Continuation-in-part of application No. 10/910,575, filed on Aug. 4, 2004, now Pat. No. 7,048,435.

(51) Int. Cl.
*G01N 25/00* (2006.01)
*G01N 17/00* (2006.01)
*G05D 21/00* (2006.01)

(52) U.S. Cl. .................. 236/44 C; 374/14; 73/865.6

(58) Field of Classification Search .............. 374/12, 374/14, 45; 236/44 A, 44 C; 73/865.6
See application file for complete search history.

(56) References Cited

U.S. PATENT DOCUMENTS 4,336,329 A    6/1982  Hesse et al.

| 5,083,558 | A | 1/1992 | Thomas et al. |
| 5,165,792 | A | 11/1992 | Crowe et al. |
| 5,368,391 | A | 11/1994 | Crowe et al. |
| 5,669,554 | A | 9/1997 | Nakamura et al. |
| 2002/0080848 | A1 | 6/2002 | Nakamura et al. |
| 2005/0123020 | A1 | 6/2005 | Nakamura |

FOREIGN PATENT DOCUMENTS

| DE | 9414990 U | 11/1994 |
| EP | 1285056 | 12/2001 |
| GB | 2416855 | 8/2006 |
| WO | 01/92460 | 12/2001 |

OTHER PUBLICATIONS

French Search Report, Dec. 15, 2006.
UK Search Report, Jan. 15, 2007.
"Use of the RH Perfusion System at elevated temperatures"; Experimental & Technical Note EN 013 a (May 2000).

*Primary Examiner*—Marc E Norman
(74) *Attorney, Agent, or Firm*—Paul, Hastings, Janofsky & Walker LLP (57) ABSTRACT

Embodiments of the present invention relate to apparatus, systems and methods for adding a humidity-controlled system to a thermogravimetric instrument. A humidity-controlled controlled chamber incorporates a housing, a humidifier, a sample chamber, a reference chamber, Peltier devices, humidity and temperature sensors, and gas transmission lines into a single unit. This single unit along with an electronic control unit and mass flow controllers provide a humidity-controlled system designed to control the atmosphere of TGA sample and reference chambers simultaneously. A system comprising an arm, motorized linear actuator an electric control unit, allows a humidity-controlled chamber to be automatically opened and closed, in turn, allowing reference and sample chambers to automatically be accessed.

38 Claims, 11 Drawing Sheets

HUMIDITY-CONTROLLED CHAMBER FOR A THERMOGRAVIMETRIC INSTRUMENT

CROSS-REFERENCE TO RELATED APPLICATIONS

The present application is a continuation-in-part of U.S. patent application Ser. No. 10/910,575, filed Aug. 4, 2004, entitled "HUMIDITY-CONTROLLED CHAMBER FOR A THERMOGRAVIMETRIC INSTRUMENT," and currently pending, the entire content of which is incorporated herein by reference.

BACKGROUND OF THE INVENTION

1. Field of the Invention

The present invention relates generally to a system used to control the humidity and temperature of a sample being tested in a thermogravimetrical analyzer (TGA). More particularly, the present invention relates to a humidity-controlled chamber designed to control the atmosphere of a TGA's sample and reference chambers simultaneously to an equal specific relative humidity level and to an equal specific temperature.

2. Background Information

A TGA is generally used to measure the decomposition of a sample as a function of temperature. The device heats a sample and measures the weight gain or loss during the process. In a typical device, a sample is suspended from a very sensitive balance. When heated, the sample undergoes a physical change. The weight versus temperature and weight versus time is then recorded and plotted for each sample. TGAs are described, for example, in U.S. Pat. No. 5,165,792, which is incorporated by reference herein. TGAs are unlike other thermal analysis apparatus (such as dynamic mechanical analyzers and some differential scanning calorimeters, for example), because the sample in the TGA needs to interact with the atmosphere.

Moisture is constantly present in our environment and can affect solid state materials due to its influence on their structural phase. This may be due to the formation of a hydrate phase or an induced amorphous to crystalline phase transition. These moisture induced changes can affect mechanical properties and can also cause chemical interactions. The effect of moisture on pharmaceutical materials, for example, can alter yield, purity, and dosage calculations.

Consequently, it is desirable to analyze materials in environments where the moisture level or humidity is controlled in addition to the temperature. An apparatus for controlling the environment of a sample for microscopic, spectroscopic, or crystallographic analysis is described in PCT Application Ser. No. WO 01/92460 (the "'460 application") by Levoguer et al., entitled "Controlled Sample Environment for Analytical Devices." This apparatus comprises a sample chamber that is fed by a gas stream having a known vapor content, which is generated by mixing two gas streams, one substantially saturated in a volatile substance and one substantially free of the volatile substance. The temperature of the apparatus, and particularly of the sample chamber, is accurately controlled and regulated by a temperature controller.

A device for thermogravimetric measurement that includes humidity control is detailed in U.S. Pat. No. 5,669,554 (the "'554 patent") by Nakamura et al. entitled "Humidity Control Thermal Analyzer" and in U.S. patent application Ser. No. US 2002/0080848 A1 (the "'848 application") by Nakamura et al. entitled "Automatic Humidity Step Control Thermal Analysis Apparatus." The device comprises a chamber for generating water vapor, a sample chamber, a heat insulating pipe, and a detector. The '554 patent and the '848 application differ primarily in their methods of controlling the sample chamber temperature and their signal control and detection.

The apparatus described in the '460 application has not been adapted for use with TGAs. The device detailed in the '554 patent and the '848 application has not been designed to work easily for standard thermal analysis. In view of the foregoing, it can be appreciated that a substantial need exists for apparatus, systems, and methods that can easily be used to adapt a standard TGA for humidity-controlled experiments in addition to standard thermal analysis.

BRIEF SUMMARY OF THE INVENTION

The present invention relates to systems and methods for adding a humidity-controlled system to a thermogravimetric instrument. One embodiment of the present invention is a humidity-controlled chamber designed to control the atmosphere of a TGA's sample and reference chambers simultaneously to an equal predetermined relative humidity (percent RH) level in a range of 5% RH to 95% RH and to an equal predetermined temperature in the range of 10° C. to 80° C. The traditional tare side hang-down is extended to create symmetry between the sample and reference pan holders, so that the sample and tare sides are influenced equally by the changes in relative humidity. Influencing the sample and tare sides equally by the changes in relative humidity eliminates an offset in weight due to a difference in relative humidity between the sample and tare sides.

A substantially saturated gas is created by bubbling a first substantially dry gas through a volatile material or by purging it through moist wicking material immersed in a bath of the volatile material. In either case, the substantially dry gas becomes substantially saturated with the volatile material. The substantially saturated gas has preferably at least 95% RH. Of course, a partially saturated gas may also be used that has between about 10% RH and about 95% RH. The substantially dry gas has preferably less than 5% RH. In at least one embodiment, the substantially saturated gas has preferably at least 99% RH, and the dry gas has preferably less than 1% RH, and more preferably less than 0.1% RH. These examples of wetness and dryness of the gases are not meant to be limiting in any way.

The humidity-controlled chamber uses three Mass Flow Controllers (MFCs). A first MFC is used to control the RH flow of a first dry gas. The second MFC is used to control the flow of the second dry gas through the humidifier, creating substantially saturated gas. A third MFC is used to control the flow of a third dry gas through the balance chamber, preventing humidified gas from entering the balance area. Gas controlled to a predetermined percent RH, or humidified gas, is created by mixing the substantially saturated gas and the first dry gas. The resultant mixture then enters the sample and reference chambers simultaneously. The humidified gas passes the pan, mixes with the dry gas from the balance chamber and then exits the system. The flow rate of the humidified gas is held constant. The design and electronic control system ensure that dry gas from the balance chamber does not mix with the humidified gas in the pan area.

A humidity sensor is placed in proximity to the sample to detect the percent RH of the sample atmosphere. In an embodiment, the sensor also serves as a feedback in a closed loop system with the first and second MFCs. Software, hardware, or both software and hardware are used to adjust the gas flow and thus the blend of substantially saturated gas and dry gas to the predetermined percent RH level.

Since the percent RH is temperature dependent, an active temperature control system operated in conjunction with a temperature sensor is used to maintain the temperature of the humidity-controlled chamber. One skilled in the art will appreciate that an active temperature control system is a device that can be used to provide both heating and cooling. In a preferred embodiment of the humidity-controlled chamber, the active temperature control system is a Peltier device (cooled by water circulation), and the temperature sensor is an embedded thermistor.

The design of the humidity-controlled chamber, incorporates the humidifier, the sample chamber, the reference chamber, the active temperature control system, the humidity sensor, the temperature sensor, and the gas transmission lines into a single unit. This single unit comprises an aluminum manifold, for example.

A TGA autosampler is an accessory that is used to automatically load samples into and unload samples from a TGA. It allows a TGA to be operated unattended for long periods of time. It typically contains a tray capable of holding multiple sample pans and a mechanism for moving these pans between the tray and the TGA.

The humidity-controlled chamber can be moved automatically. The humidity-controlled housing is mounted on an arm and the arm is mounted to a motorized linear actuator. This allows the chamber to be opened automatically and the sample to be replaced. This can be done with or without the use of an autosampler. It is also done while controlling the chamber's temperature and percent RH. The movement of the chamber also allows its replacement with another type of furnace. This provides the user with the flexibility to tailor the instrument to the type of study and increases the overall utilization of the instrument.

One skilled in the art will appreciate that the invention is not limited in its application to the details of construction, the arrangements of components, and the arrangement of steps set forth in the following detailed description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

Figure 1A:
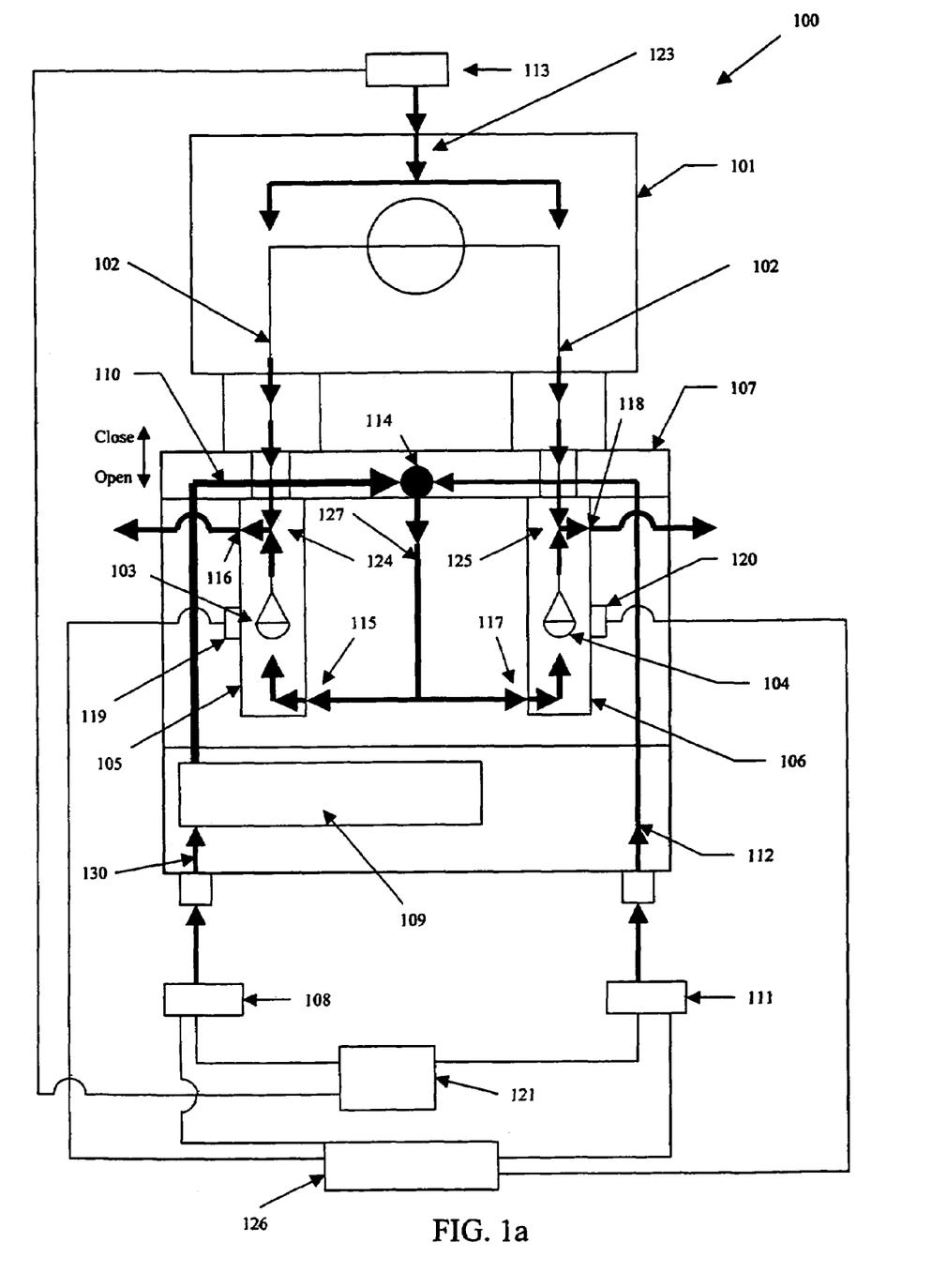
FIG. 1a is a schematic diagram of a frontal view of an exemplary humidity-controlled system for use by a TGA showing the internals of the humidity-controlled chamber, in accordance with an embodiment of the present invention.

FIG. 1a is a schematic diagram of a frontal view of an exemplary humidity-controlled system for use by a TGA showing the internals of the humidity-controlled chamber, in accordance with an embodiment of the present invention. The balance chamber 101, hang-down hooks 102, reference pan 103, and sample pan 104 of a TGA are shown. The atmospheres of reference chamber 105 and sample chamber 106 are controlled, because they are housed within humidity-controlled chamber housing 107. The atmospheres of reference chamber 105 and sample chamber 106 are simultaneously controlled to an equal percent RH level in a range of about 5% RH to about 95% RH and to an equal specific temperature in the range of about 10° C. to about 80° C.

Humidity-controlled system 100 uses three MFCs. Gas supply 121 is a source of substantially dry gas, or gas that is substantially free of a volatile material. Preferably, the substantially dry gas has less than about 5% RH. In an embodiment, the substantially dry gas has preferably less than about 1% RH, and more preferably less than about 0.1% RH. As non-limiting examples, nitrogen or air can be used for the dry gas. Other inert gases may also be used, but the relative humidity and flow sensors must be calibrated accordingly. The inert gases include helium (He), neon (Ne), argon (Ar), krypton (Kr), xenon (Xe) and radon (Rn).

A first MFC, 111, is used to control the flow of a first dry gas 112, or gas that is substantially free of the volatile material, through the humidity-controlled chamber.

A second MFC, 108, is used to control the flow of a second dry gas 130 through the humidifier 109, creating a substantially saturated gas 110. This substantially saturated gas may be created by bubbling the second dry gas through a volatile material, such as water, or alternatively by purging the second dry gas through a moist wicking material immersed in a bath of the volatile material. Preferably the substantially saturated gas 110 has greater than about 95% RH. In an embodiment, the substantially saturated gas preferably has greater than about 99% RH. In an embodiment, a partially saturated gas is created with the humidifier 109. The partially saturated gas has between about 10% RH and about 95% RH. Additionally, organic liquid (e.g., alcohol or ether) can be used instead of water. However, in the case of an organic liquid, a relative humidity sensor is not used, and the relative saturation is approximated by using the proportion between the dry and substantially saturated flow.

A third MFC, 113, is used to control the flow of a third dry gas through the balance chamber 101, preventing humidified gas 127 from entering the balance area. Dry gas 123 moves through the balance area and exits via sample chamber gas outlet 118 and reference chamber gas outlet 116.

Humidified gas 127, or the gas controlled to a predetermined target content of the volatile material, is created from mixing substantially saturated gas 110 and first dry gas 112 in manifold 114 and enters reference chamber 105 and sample chamber 106 simultaneously. Humidified gas 127 enters reference chamber 105 at gas inlet 115, passes reference pan 103, mixes with dry gas 123 from balance chamber 101 at location 124, and then exits through gas outlet 116. Likewise, humidified gas 127 enters sample chamber 106 at gas inlet 117, passes sample pan 104, mixes with dry gas 123 from balance chamber 101 at location 125, and then exits through gas outlet 118. The design and control of system 100 ensure that dry gas 123 from balance chamber 101 does not mix with humidified gas 127 in the reference or sample pan areas.

Humidity sensors 119 and 120 are placed in close proximity to reference pan 103 and sample pan 104, respectively. In an embodiment, humidity sensor 120 also serves as feedback in a closed loop with the MFCs 108 and 111. Software, hardware, or both software and hardware of electronic control unit 126 is used to retrieve the humidity measured by humidity sensor 120, to compare this measured humidity to a target percent RH level, and to adjust MFCs 108 and 111 to control the blend of substantially saturated gas 110 and the dry gas 112 in response to this comparison. A user provides the target percent RH level to the software, hardware, or both software and hardware via a user interface of the TGA.

Humidity sensor 119 is used to test whether or not the humidity in reference chamber 105 agrees with the humidity in sample chamber 106. If humidity sensors 119 and 120 do not agree within a certain threshold (e.g., four percentage points of RH, based on each sensor providing +/−2% RH), a warning is posted on the user interface of the TGA or the test is terminated. In a preferred embodiment, the user is able to select one of these two warning options via a software, hardware, or both software and hardware driven option menu. Also, in a preferred embodiment the measurements of humidity sensors 119 and 120 are compared by electronic control unit 126.

In an embodiment that includes a closed loop system, if the percent RH measured by sensor 120 is not equal to the target percent RH level entered by the user within a predetermined threshold, the software, hardware, or both software and hardware may adjust the percent of RH of saturated gas 127 by adjusting the output of MFC 108 and MFC 111. In one exemplary embodiment, if measured percent RH of humidified gas 127 is less than the target percent RH level, then the software, hardware, or both software and hardware will signal MFC 108 to output more gas and MFC 111 to output proportionally less gas. Similarly, if the measured percent RH of saturated gas 127 is more than the target percent RH level, then the software, hardware, or both software and hardware will signal MFC 108 to output less gas and MFC 111 to output proportionally more gas. In both cases, the flow rate through the sample and reference chambers is held constant. The flow rate of MFC 113 is also held constant. In another embodiment, the target percent RH level is varied during an experiment and is pre-programmed by a user before an experiment using the electronic control unit.

In another embodiment, the humidity in reference chamber 105 and sample chamber 106 is controlled with an open loop system. In this embodiment, the target humidity is entered by the user via the user interface. The ratio of the mass flow rates for the dry gas 112 and the saturated gas 110 in order to provide the humidified gas 127 are calculated by the electronic control unit based on the target humidity. For example, if the target humidity is 25% RH, the electronic control unit calculates that a ratio of 3:1 (dry gas 112 and saturated gas 110) is needed, and signals MFC 108 and MFC 111 to adjust the flow rates of the gas streams accordingly. Humidity sensors 119, 120 may be used to verify the humidity in reference chamber 105 and sample chamber 106, respectively, but no feedback is used to automatically control MFC 108 and MFC 111. In embodiments where MFC 108 is located before the humidifier 109, the temperature of the humidity-controlled chamber may be used to further adjust the ratio of the flow rates of the dry gas 112 and the saturated gas 110 in order to account for the mass of the volatile material that is picked up by the saturated gas 110 in the humidifier 109. Because the amount of volatile material that is needed to saturate a gas is dependent on the temperature, the ratio of the mixture (flow rates) of the dry gas 112 and the saturated gas 110 should be adjusted accordingly. In an embodiment, the electronic control unit uses the temperature of the humidity-controlled chamber to calculate the theoretical increase of the mass of the saturated gas 110, and adjusts the ratio of the mixture (flow rates) based on the calculated increase. In an embodiment, the electronic control unit may be configured to calculate the theoretical increase in mass based on the volatile material and gas being used. In this embodiment, the user may input the volatile material and/or gas being used so that the electronic control unit executes the correct program and/or looks up the correct look-up table to calculate the theoretical increase in mass due to an increase in temperature, and adjust the flow rates of the dry gas 112 and the saturated gas 110 accordingly.

Since the target percent RH level of humidified gas 127 is temperature dependent, it is important to control the temperature of the humidity-controlled chamber. In one embodiment, a user provides a target temperature. The target temperature is entered through the user interface of the TGA. The target temperature is maintained by an active temperature control system placed in proximity to reference chamber 105 and sample chamber 106. A temperature sensor is placed between reference chamber 105 and sample chamber 106. The active temperature control system adjusts the temperature of the humidity-controlled chamber to within about 0.1 degree Celsius of the target temperature. The active temperature control system and the temperature sensor are controlled and monitored, respectively, by electronic control unit 126.

Figure 1B:
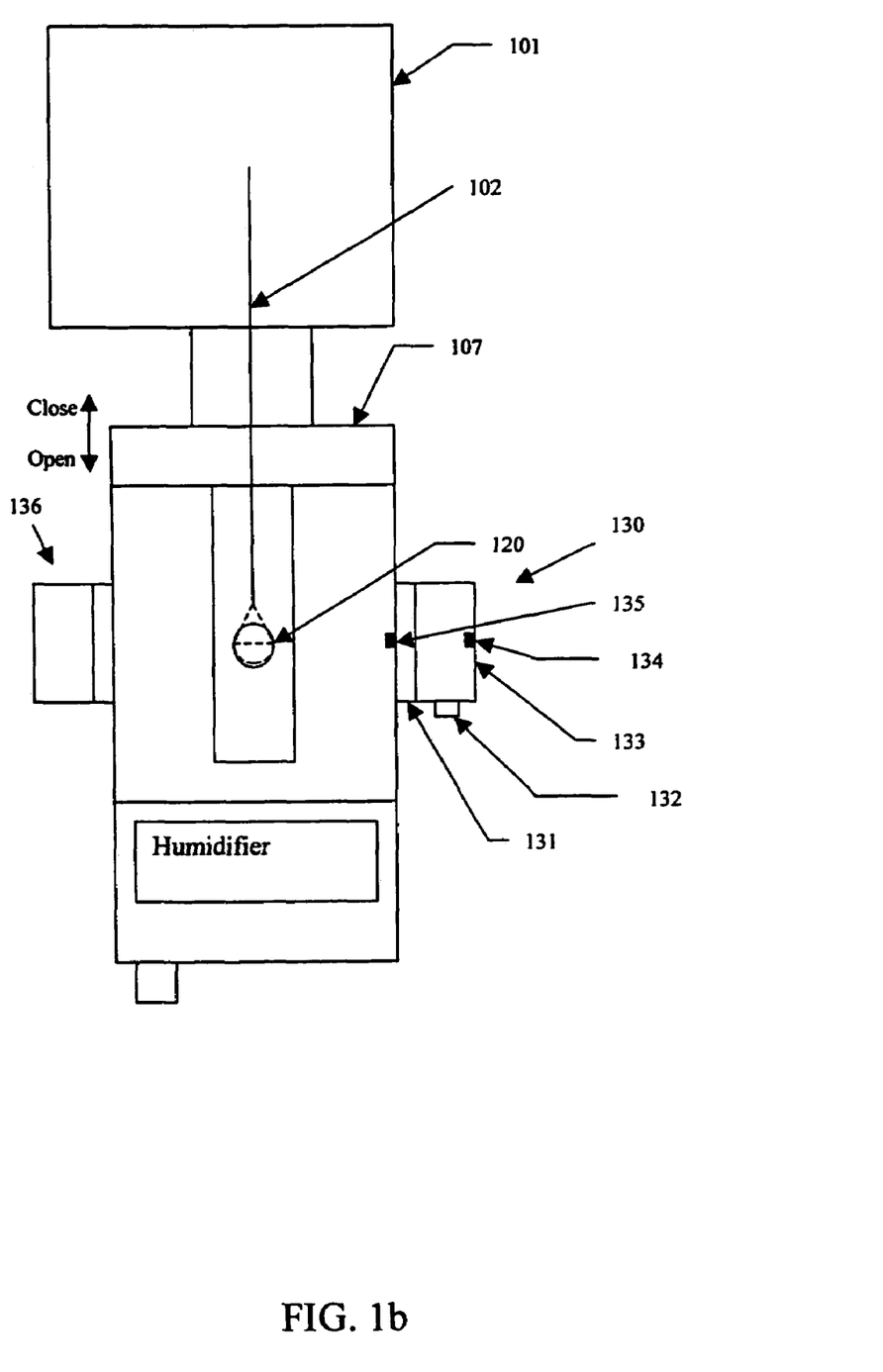
FIG. 1b is a schematic diagram of a profile view of a humidity-controlled system for use by a TGA showing the sensors and Peltier devices attached to the humidity-controlled chamber, in accordance with an embodiment of the present invention.
Figure 1C:
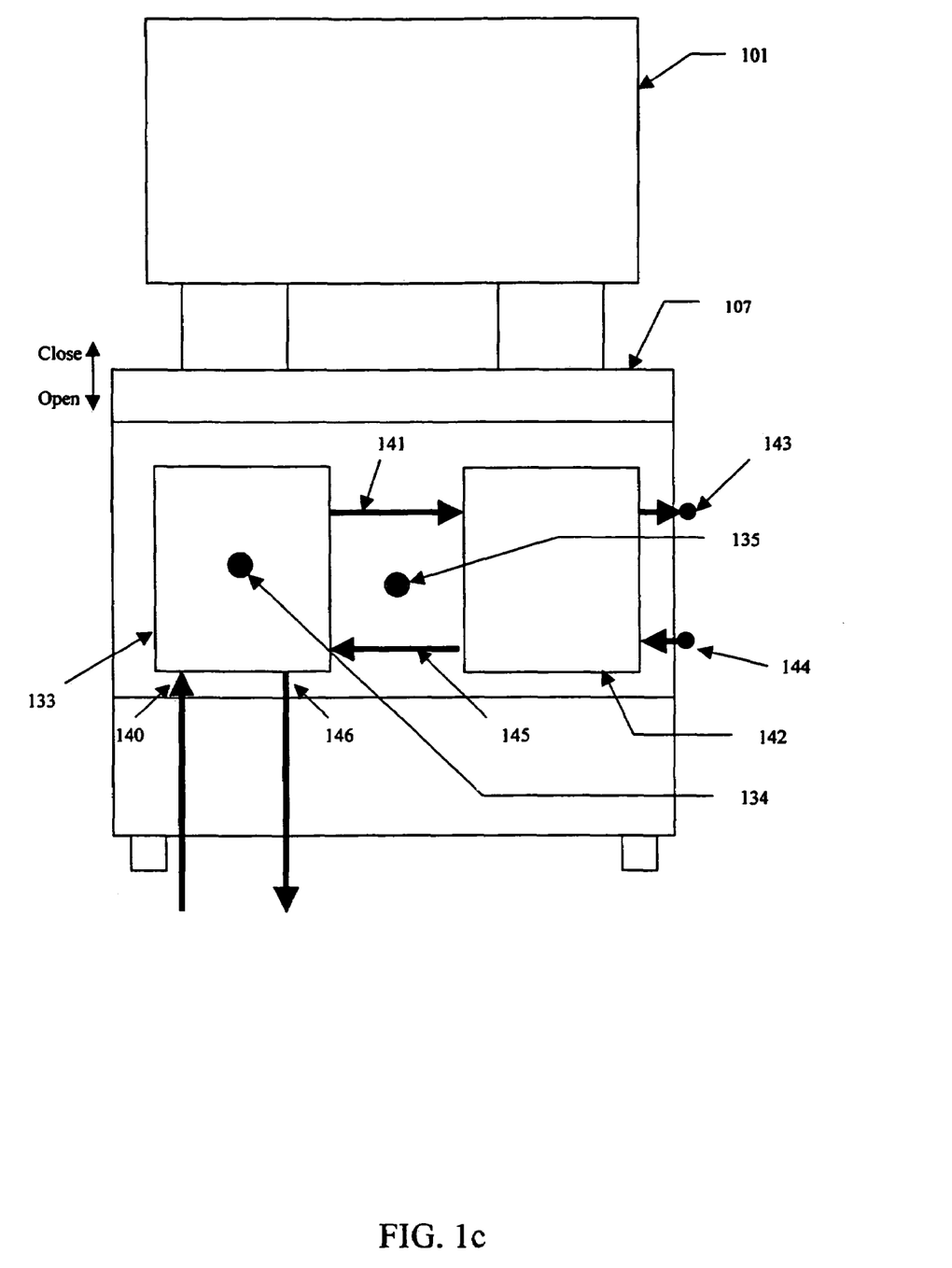
FIG. 1c is a schematic diagram of a frontal view of a humidity-controlled system for use by a TGA showing the water cooling flow through the Peltier devices attached to the humidity-controlled chamber, in accordance with an embodiment of the present invention.

In another embodiment, Peltier devices and a housing temperature control thermistor are used to control the temperature of the humidity-controlled chamber. FIG. 1b is a schematic diagram of a profile view of a humidity-controlled system for use by a TGA showing the sensors and Peltier devices attached to the humidity-controlled chamber, in accordance with an embodiment of the present invention. On one side of the chamber is Peltier device 130. This device includes Peltier thermoelectric heat pump 131, water cooling connection 132, water cooling block 133, and Peltier safety thermistor 134. Also shown in the figure are housing temperature control thermistor 135 and humidity sensor 120. On the other side of the chamber is a second Peltier device 136. Four Peltier devices (only two are shown) are used in the embodiment of FIG. 1b to achieve temperature uniformity. The Peltier devices and housing temperature control thermistor 135 are used to control the temperatures of the reference and sample chambers. There is one housing temperature control thermistor 135 that is mounted centered between the reference and sample chambers (as shown in FIG. 1c). One Peltier safety thermistor 134 is mounted at the center of one of the water cooling blocks to prevent damage to the Peltier devices.

The electronic control unit of the TGA (shown as 126 in FIG. 1a) is used to control the Peltier devices and to monitor housing temperature control thermistor 135. The electronic control unit measures the temperature of the housing by reading housing temperature control thermistor 135. The target temperature of the housing is input by the user to the electronic control unit via the TGA user interface. The electronic control unit compares the temperature measured at thermistor 135. If this measurement differs from the target temperature, the electronic control unit adjusts the electric signal to the Peltier devices to increase or decrease the amount of heat pumped. In one embodiment, if the temperature of the housing as measured by thermistor 135 is less than the target temperature, then the Peltier devices are signaled to pump heat to the housing. Similarly, if the temperature of the housing as measured by thermistor 135 is greater than the target temperature, then the Peltier devices are signaled to pump heat away from the housing.

When Peltier devices are used to cool the humidity-controlled chamber, they pump heat from the chamber to the water cooling blocks, which, in turn, are cooled by water circulated through their cooling blocks. All of the cooling blocks of the Peltier devices used in the humidity-controlled system are connected and receive the same water cooling flow. FIG. 1c is a schematic diagram of a frontal view of a humidity-controlled system for use by a TGA showing the water cooling flow through the Peltier devices attached to the humidity-controlled chamber, in accordance with an embodiment of the present invention. Cooling water enters at water cooling inlet 140 and circulates through Peltier cooling block 133. The cooling water then flows from Peltier cooling block 133 to Peltier cooling block 142 through 141. After circulating through cooling block 142 the cooling water flows to the other side of the humidity-controlled chamber housing 107 at 143, and similarly flows through the cooling blocks of the two Peltier devices on the other side of housing 107. The cooling water returns from the other side of housing 107 at 144, flows from cooling block 142 to cooling block 133 through 145, and exits cooling block 133 and the system at water cooling outlet 146.

Peltier devices can also be used to heat the humidity-controlled chamber. When this happens the Peltier devices pump heat from the water cooling blocks to the humidity-controlled chamber. In this case, the circulating water supplies heat to the cooling blocks to replace heat pumped into the humidity-controlled chamber. This is done by reversing the current flow in the Peltier devices. The electronic control unit 126 supplies varying amounts of current of either polarity to the Peltier devices to pump heat into or out of the humidity-controlled chamber as needed to maintain the desired temperature.

An exemplary design of the humidity-controlled system incorporates a humidifier, a reference chamber, a sample chamber, Peltier devices, a humidity sensor, a temperature sensor, and gas transmission lines into a single humidity-controlled chamber housing. This housing comprises an aluminum manifold, for example. The single unit design of the humidity-controlled chamber has numerous advantages. First, it obviates the need for additional apparatus to reduce the effects of the ambient environment on the humidity generating equipment. For example, the '554 patent and '848 application require a heat insulation pipe to prevent dew condensation. Second, it allows the humidity-controlled chamber to be moved automatically. This enables the sample chamber to be loaded and unloaded automatically. Third, it allows the entire chamber to be easily replaced with another type of furnace. This provides the user with the flexibility to tailor the instrument to a particular type of study and to increase the overall utilization of the instrument.

Figure 2:
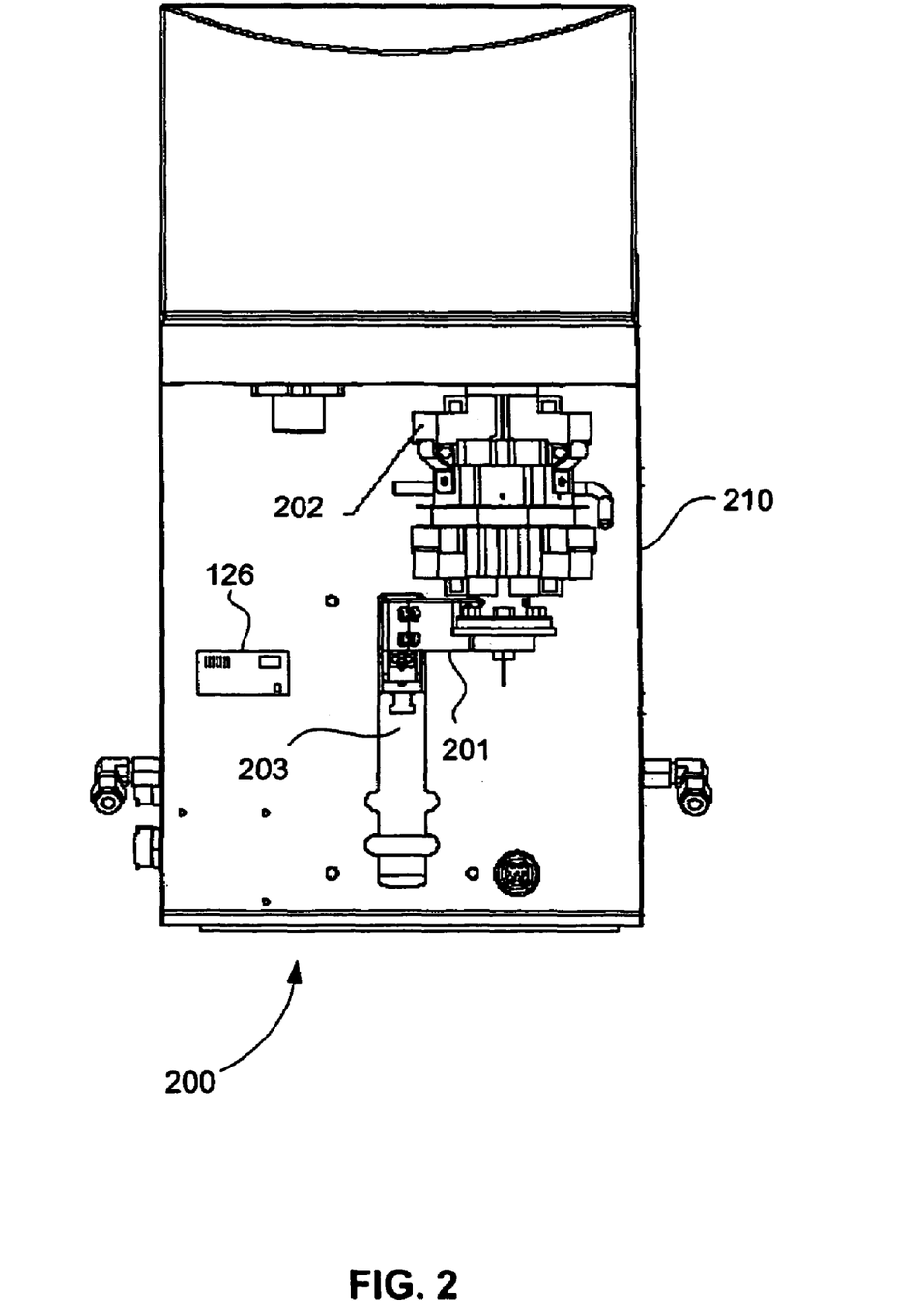
FIG. 2 is a schematic diagram of a TGA containing a system allowing for replacement of different types of furnaces, in accordance with an embodiment of the present invention.

FIG. 2 is a schematic diagram of a TGA containing a system allowing for replacement of different types of furnaces, in accordance with an embodiment of the present invention. System 200 includes armature 201, furnace housing 202, motorized linear actuator 203, electronic control unit 126, and TGA frame 210. Furnace housing 202 is attached to armature 201. Armature 201 is attached to motorized linear actuator 203. Motorized linear actuator 203 and electronic control unit 126 are mounted to TGA frame 210. Motorized linear actuator 203 is electrically connected (not shown) to electronic control unit 126. In FIG. 2, a standard temperature-only TGA furnace housing 202 is shown in the closed position. In order to open the furnace, linear actuator 203 is engaged and moves furnace housing 202 downward, allowing sample access. Alternatively, a humidity-controlled chamber can be mounted to the arm 201. One skilled in the art will appreciate that a humidity-controlled chamber is a type of TGA furnace.

Figure 3A:
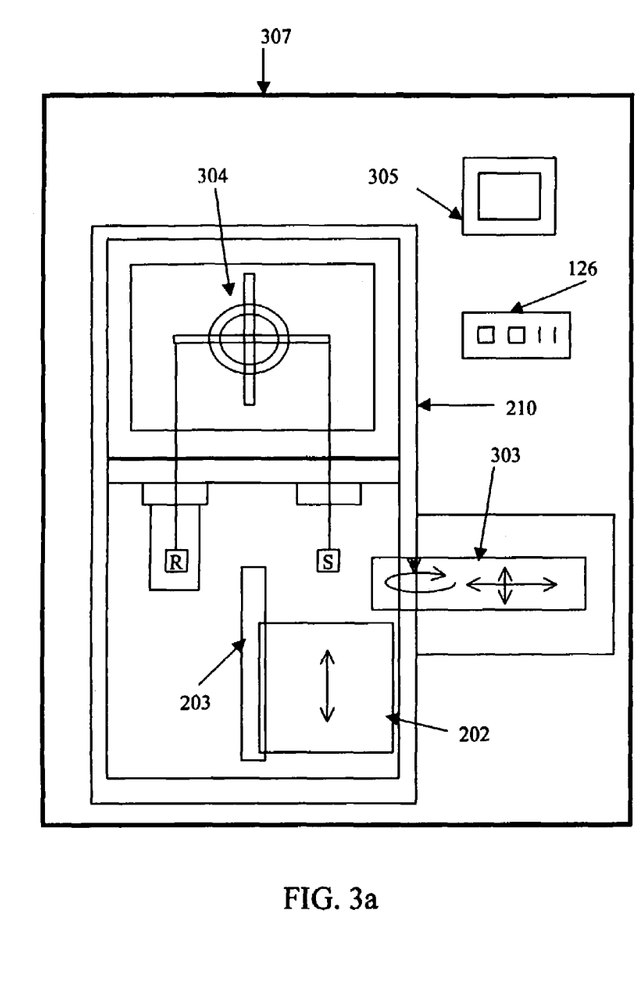
FIG. 3a is a schematic diagram showing a TGA containing a temperature-only furnace, in accordance with an embodiment of the present invention.
Figure 3B:
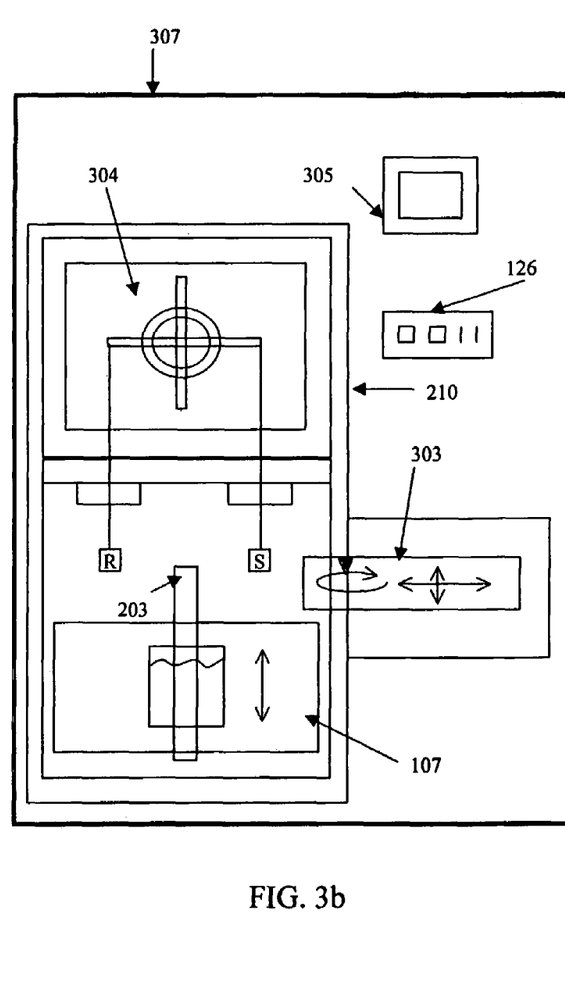
FIG. 3b is a schematic diagram showing a TGA containing a humidity-controlled chamber, in accordance with an embodiment of the present invention.

FIG. 3a is a schematic diagram showing a TGA containing a temperature-only furnace, in accordance with an embodiment of the present invention. Standard TGA furnace housing 202 is shown mounted to linear actuator 203. FIG. 3b is a schematic diagram showing a TGA containing a humidity-controlled chamber, in accordance with an embodiment of the present invention. Humidity-controlled chamber housing 107 is shown mounted to linear actuator 203. Both of FIGS. 3a and 3b show how the sample can be loaded or unloaded by automatically moving the furnace or humidity-controlled chamber up or down. This can be done with or without autosampler 303. Other parts of the TGA include balance 304, interactive display 305, electronic control unit 126, frame 210, and cabinet 307.

Figure 4:
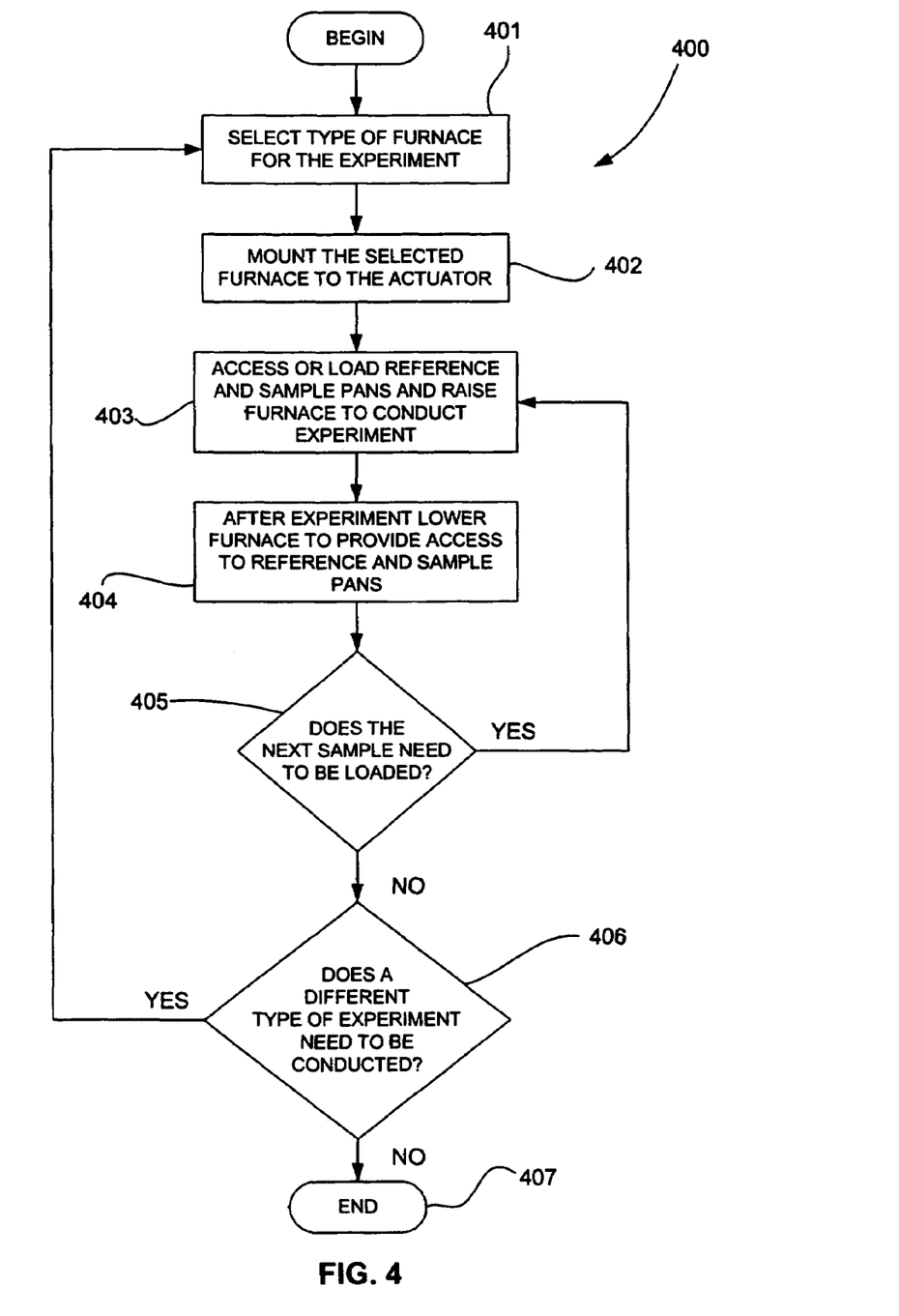
FIG. 4 is a flowchart showing a loading method of the humidity-controlled chamber, in accordance with an embodiment of the present invention.

FIG. 4 is a flowchart showing an exemplary method for loading the humidity-controlled chamber, in accordance with an embodiment of the present invention.

In step 401 of method 400, the type of furnace for an experiment is selected. A humidity-controlled chamber would be selected for an experiment to measure the effects of moisture on a pharmaceutical, for example.

In step 402, the furnace is mounted to the motorized linear actuator of the TGA.

In step 403, the sample and reference pans of the TGA are then loaded and the furnace is raised to conduct the experiment.

In step 404, the furnace is lowered under the control of the electronic control unit. Lowering the furnace provides access to the reference and sample pans.

In step 405, a decision is then made. If a series of samples are being tested, the next sample can be loaded, and the method returns to step 403.

In step 406, after all the samples have been tested, another decision is then made. If a different type of experiment is to be conducted, the process returns to step 401. Otherwise, the process ends at step 407.

Figure 5:
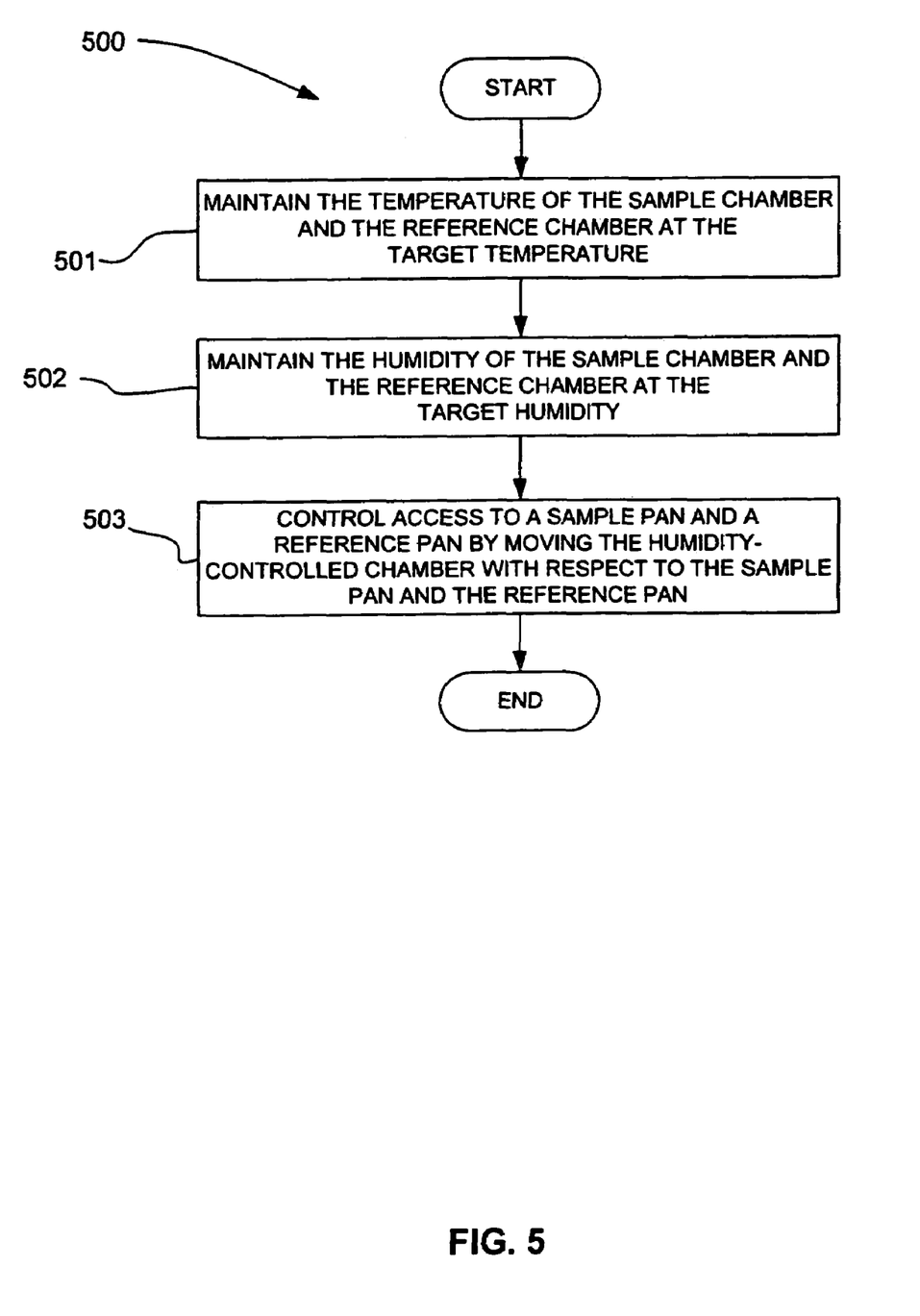
FIG. 5 is a flowchart of a method for controlling a humidity-controlled chamber using an electronic control unit of a thermogravimetric instrument, in accordance with an embodiment of the present invention.

FIG. 5 is a flowchart of a method for controlling a humidity-controlled chamber using an electronic control unit of a thermogravimetric instrument, in accordance with an embodiment of the present invention.

In step 501 of method 500, the temperature of the sample chamber and the reference chamber of the humidity-controlled chamber is maintained substantially at a target temperature.

In step 502, the humidity of the sample chamber and the reference chamber is maintained at substantially a target humidity.

In step 503, access to the sample pan and the reference pan of the thermogravimetric instrument is controlled by moving the humidity-controlled chamber with to the sample pan and the reference pan.

Figure 6:
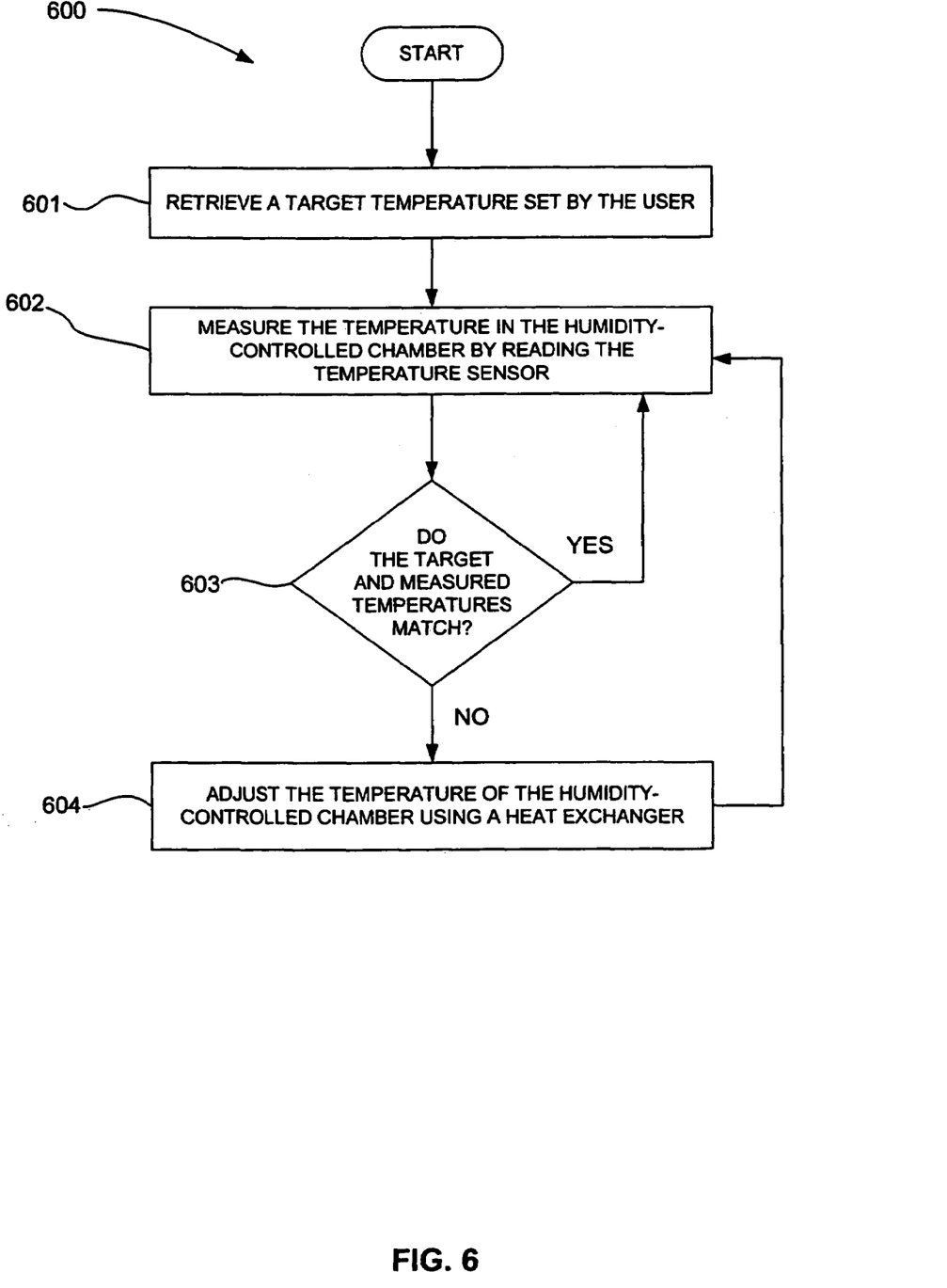
FIG. 6 is a flowchart of a method for controlling the temperature of a humidity-controlled chamber using an electronic control unit of a thermogravimetric instrument, in accordance with an embodiment of the present invention.

FIG. 6 is a flowchart of a method for controlling the temperature of a humidity-controlled chamber using the electronic control unit of a thermogravimetric instrument, in once with an embodiment of the present invention.

In step 601 of method 600, a target temperature for the humidity-controlled is set by a user. The user enters this information into the electronic control unit the user interface of the TGA. In one embodiment of this method, the target sure does not vary with time. In another embodiment of this method, the target temperature varies with time.

In step 602, the temperature in the humidity-controlled chamber is measured. The electronic control unit measures this temperature by reading the temperature sensor in the humidity controlled-chamber.

In step 603, the measured temperature is compared to the target temperature.

In step 604, the active temperature control system attached to the humidity-controlled chamber adjusts the temperature of the humidity-controlled chamber if the measured temperature and the target temperature do not correspond within a predetermined temperature threshold. An exemplary predetermined temperature threshold is 0.1 degree Celsius. In another embodiment, the temperature of the humidity-controlled chamber is adjusted by Peltier devices.

The steps of method 600 are executed as long as the temperature of the humidity-controlled chamber is maintained. In one embodiment of this method, this temperature is maintained during replacement of sample and reference pans and throughout more than one experiment.

Figure 7:
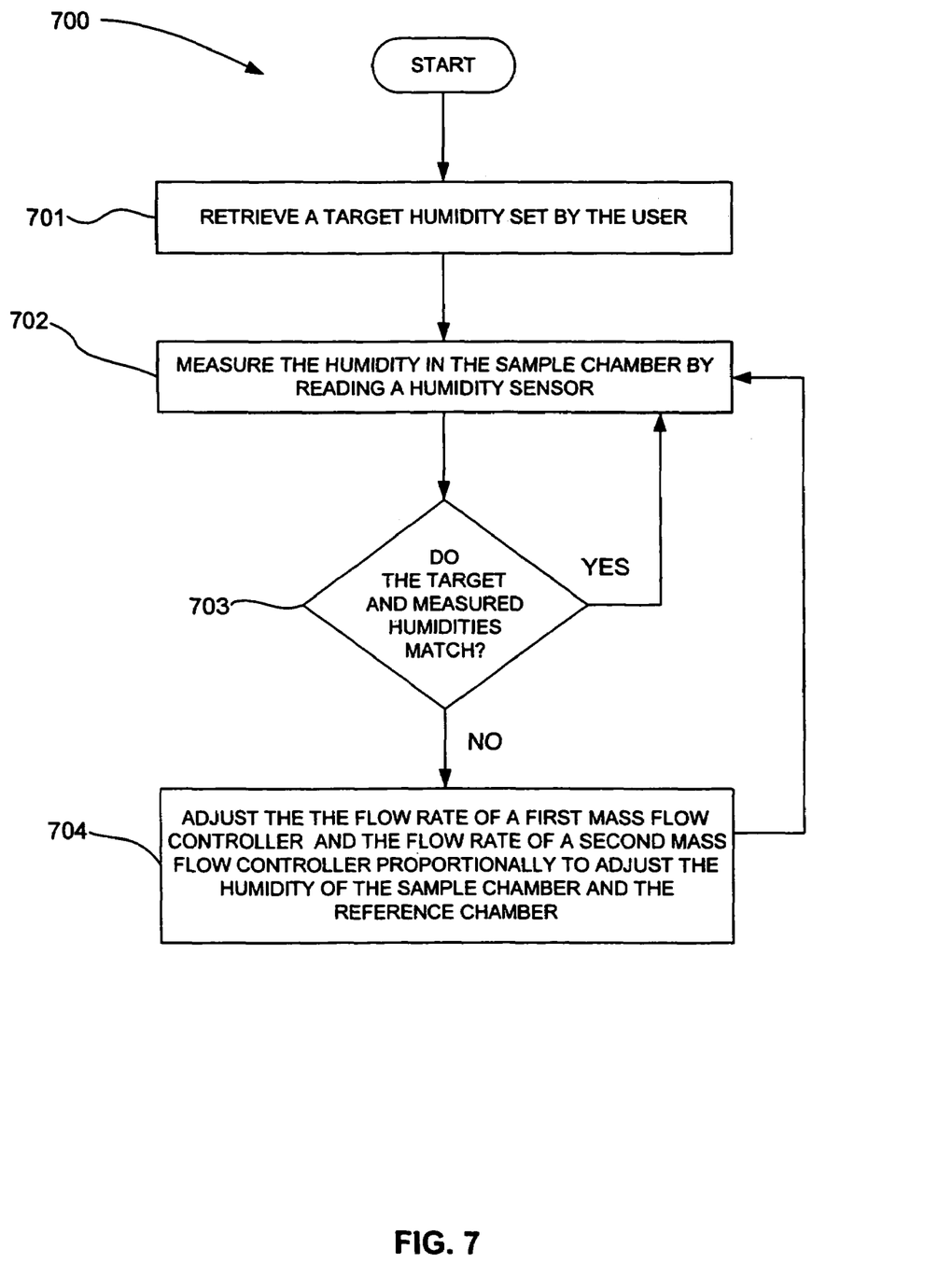
FIG. 7 is a flowchart of a method for controlling the humidity of a humidity-controlled chamber using an electronic control unit of a thermogravimetric instrument, in accordance with an embodiment of the present invention.

FIG. 7 is a flowchart of a method 700 for controlling the humidity of a humidity-controlled chamber using an electronic control unit of a thermogravimetric instrument, in accordance with an embodiment of the present invention.

In step 701 of method 700, a target humidity for the humidity-controlled chamber is set by a user. The user enters this information into the electronic control unit through the user interface of the TGA. In one embodiment of this method, the target humidity does not vary with time. In another embodiment of this method, the target humidity varies with time.

In step 702, the humidity in the humidity-controlled chamber is measured. The electronic control unit measures this humidity by reading the humidity sensor in proximity to the sample chamber of the humidity controlled-chamber.

In step 703, the measured humidity is compared to the target humidity.

In step 704, the flow rate of a first mass flow controller is adjusted and the flow rate of a second mass flow controller is proportionally adjusted to adjust the humidity of the reference chamber and the sample chamber, if the target humidity is not substantially equivalent to the measured humidity. The first mass flow controller provides a first gas stream substantially free of a volatile material. The second mass flow controller mixes a second gas stream substantially free of the volatile material with the volatile material to produce a gas stream substantially saturated by the volatile material. The first gas stream and the saturated gas stream are mixed in a manifold to produce a humidified gas stream that passes through the sample chamber and the reference chamber. The flow rates of the first mass flow controller and the second mass flow controller are adjusted so that the flow rate of the humidified gas stream remains constant.

The steps of method 700 are executed as long as the humidity of the humidity-controlled chamber is maintained.

Figure 8:
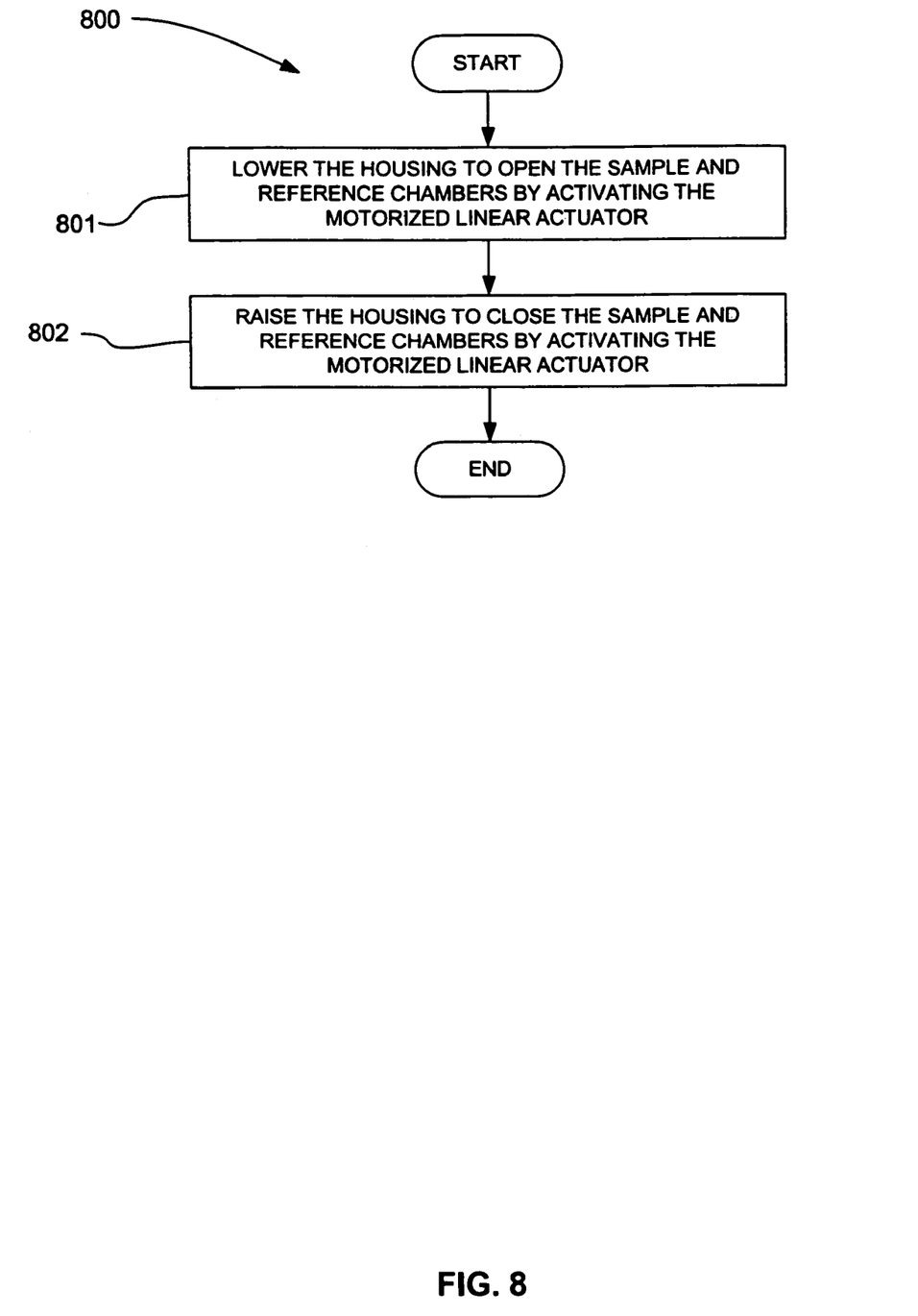
FIG. 8 is a flowchart of a method for controlling access to a sample pan and a reference pan during an experiment by an electronic control unit in a humidity-controlled system of a thermogravimetric instrument, in accordance with an embodiment of the present invention.

FIG. 8 is a flowchart of a method for controlling access to a sample chamber and a reference chamber during an experiment by an electronic control unit in a humidity-controlled system of a thermogravimetric instrument in accordance with an embodiment of the present invention.

In step 801 of method 800, a housing of the humidity-controlled system is lowered to open the sample chamber and the reference chamber. This is accomplished by activating a motorized linear actuator. The housing is mounted to an armature of the motorized linear actuator.

In step 802, the housing of the humidity-controlled system is raised to close the sample chamber and the reference chamber. This is accomplished by activating the motorized linear actuator. Steps 801 and 802 are required to load a new sample or reference.

Figure 9:
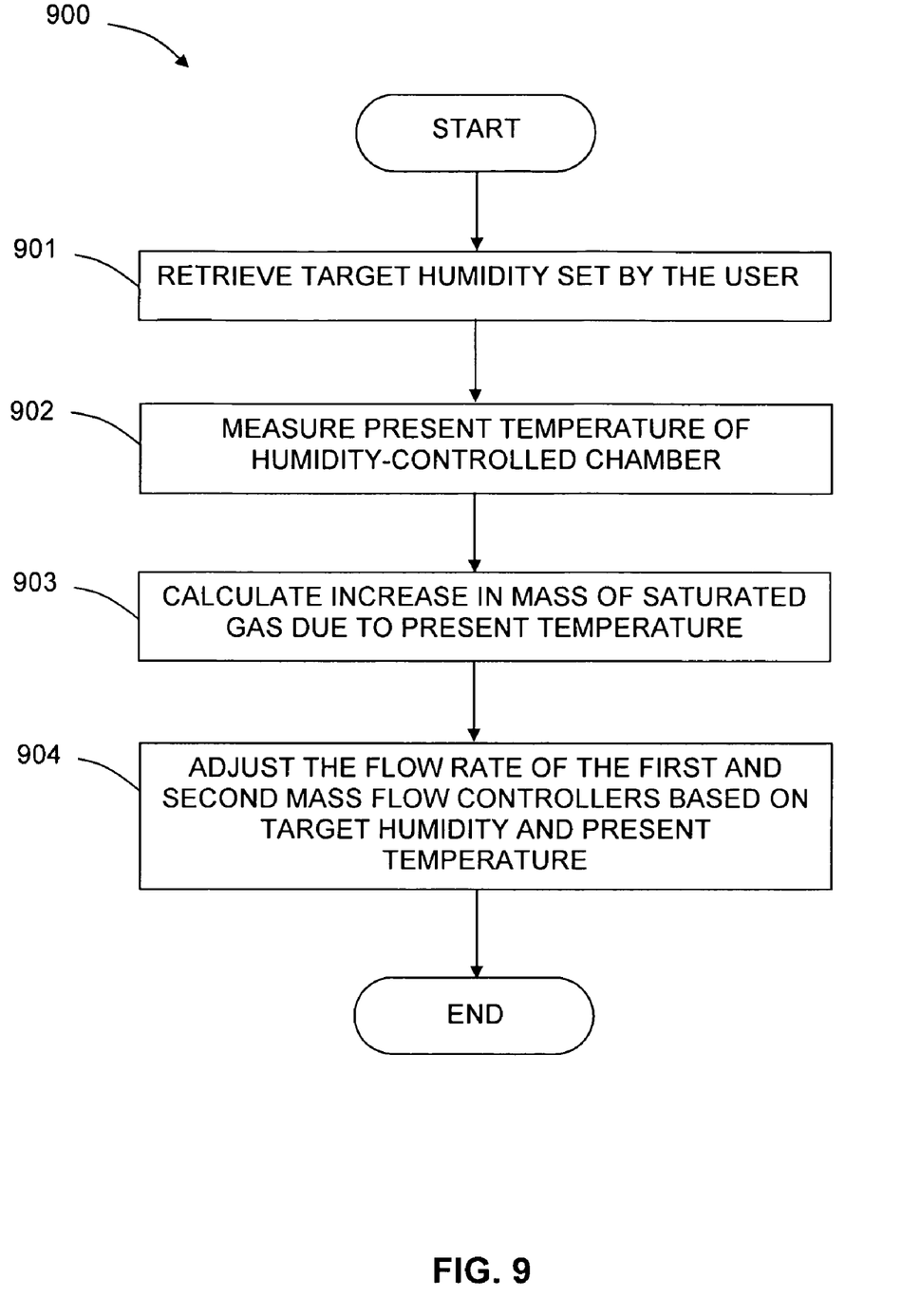
FIG. 9 is a flowchart of a method for controlling the humidity of a humidity-controlled chamber using an electronic control unit of a thermogravimetric instrument, in accordance with another embodiment of the present invention.

FIG. 9 is a flowchart of a method 900 for controlling the humidity of a humidity-controlled chamber using an electronic control unit of a thermogravimetric instrument, in accordance with an embodiment of the present invention.

In step 901 of method 900, a target humidity for the humidity-controlled chamber is set by a user. The user enters this information into the electronic control unit through the user interface of the TGA. In one embodiment of this method, the target humidity does not vary with time. In another embodiment of this method, the target humidity varies with time.

In step 902, a temperature of the humidity-controlled chamber is measured with a temperature sensor.

In step 903, the electronic control unit calculates a theoretical increase in mass of the saturated gas due to the present temperature of the humidity-controlled chamber, as measured by the temperature sensor.

In step 904, the flow rate of a first mass flow controller is adjusted and the flow rate of a second mass flow controller is proportionally adjusted to adjust the humidity of the reference chamber and the sample chamber. The first mass flow controller provides a first gas stream substantially free of a volatile material. The second mass flow controller mixes a second gas stream substantially free of the volatile material with the volatile material to produce a gas stream substantially saturated by the volatile material. The first gas stream and the saturated gas stream are mixed in a manifold to produce a humidified gas stream that passes through the sample chamber and the reference chamber. The flow rates of the first mass flow controller and the second mass flow controller are adjusted so that the calculated theoretical increase in the mass of the saturated gas stream is account for and so that the flow rate of the humidified gas stream remains constant.

The apparatus, systems, and methods in accordance with an embodiment of the present invention disclosed herein can advantageously improve the utilization of a TGA. The present invention allows the percent RH and temperature of the sample and reference chambers to be controlled. It allows for computer-controlled access to the sample and reference chambers to replace the sample or reference pan. It works in conjunction with an autosampler. The design provides the ability to control the sample chamber's percent RH while the sample is being replaced. The entire humidity-controlled chamber is designed as a small self-contained package. This design allows it to easily be replaced with another type of furnace.

Embodiments of an apparatus, system, and method for adding a humidity-controlled chamber to a TGA have been described. In the foregoing description, for purposes of explanation, numerous specific details are set forth to provide a thorough understanding of the present invention. It will be appreciated, however, by one skilled in the art that the present invention may be practiced without these specific details. In other instances, structures and devices are shown in block diagram form. Furthermore, one skilled in the art can readily appreciate that the specific sequences in which methods are presented and performed are the illustrative and it is contemplated that the sequences can be varied and still remain within the spirit and scope of the present invention.

In the foregoing detailed description, apparatus, systems, and methods in accordance with embodiments of the present invention have been described with reference to specific exemplary embodiments. Accordingly, the present specification and figures are to be regarded as illustrative rather than restrictive. The scope of the invention is to be defined by the claims appended hereto, and by their equivalents.

What is claimed is:

1. A humidity-controlled system for a thermogravimetric instrument comprising:
   a humidity-controlled chamber comprising a sample chamber and a reference chamber; and
   an electronic control unit configured to (1) control a flow of a substantially dry gas and a flow of an at least partially saturated gas to the sample chamber and the reference chamber, a ratio of the flows of the substantially dry gas and the at least partially saturated gas being based on a target humidity, and (2) control access to the sample chamber and the reference chamber by controlling movement of the humidity-controlled chamber.

2. A humidity-controlled system according to claim 1, further comprising: a temperature sensor disposed in the humidity-controlled chamber, wherein the electronic control unit is further configured to adjust the ratio of the flows of the substantially dry gas and the at least partially substantially saturated gas based on the temperature sensed by the temperature sensor.

3. The humidity-controlled system of claim 2, wherein the system is configured to calculate a theoretical increase in mass of the at least partially saturated gas due to an increase in temperature, and to adjust the flow of the substantially dry gas and the at least partially saturated gas based upon the calculated theoretical increase in mass.

4. The humidity controlled system of claim 3, wherein the at least partially saturated gas is obtained by exposing a first substantially dry gas to a volatile material, wherein the theoretical increase in mass of the at least partially saturated gas is based upon one or more of the specific first substantially dry gas and the specific volatile material being used.

5. The humidity controlled system of claim 4, wherein the electronic control unit is configured to perform at least one of (a) executing a program according to at least one of the first substantially dry gas and the volatile material and (b) performing a look up in a look-up table corresponding to least one of the first substantially dry gas and the volatile material.

6. A humidity-controlled system according to claim 1, further comprising: a humidity sensor disposed in the humidity-controlled chamber for sensing the humidity of the humidity-controlled chamber, wherein the electronic control unit is further configured to adjust the ratio of the flows of the substantially dry gas and the at least partially saturated gas based on a difference between the target humidity and the humidity sensed by the humidity sensor.

7. A humidity-controlled system according to claim 1, further comprising: an active temperature control system proximate to the sample chamber and the reference chamber; and a temperature sensor placed between the sample chamber and the reference chamber, wherein the electronic control unit is further configured to control the temperature of the sample chamber and the reference chamber.

8. A humidity-controlled system according to claim 7, wherein the electronic control unit is configured to control the temperature by obtaining a temperature measurement from the temperature sensor and controlling the active temperature control system in response to the temperature measurement.

9. A humidity-controlled system according to claim 1, further comprising: an actuator connected to the humidity-controlled chamber, wherein the electronic control unit is configured to control access to the sample chamber and the reference chamber by controlling the actuator to move the humidity-controlled chamber relative to the sample chamber and the reference chamber.

10. A humidity-controlled system according to claim 1, wherein the substantially dry gas has a relative humidity of less than about 5%.

11. A humidity-controlled system according to claim 10, wherein the substantially dry gas has a relative humidity of less than about 1%.

12. A humidity-controlled system according to claim 11, wherein the substantially dry gas has a relative humidity of less than about 0.1%.

13. A humidity-controlled system according to claim 1, wherein the at least partially saturated gas has a relative humidity of greater than about 10%.

14. A humidity-controlled system according to claim 13, wherein the at least partially saturated gas is a substantially saturated gas having a relative humidity of greater than about 95%.

15. A humidity-controlled system according to claim 14, wherein the substantially saturated gas has a relative humidity of greater than about 99%.

16. A method for controlling an atmosphere within a sample chamber and a reference chamber in a thermogravimetric instrument, the method comprising: flowing a mixture of a substantially dry gas and an at least partially saturated gas to a humidity-controlled chamber that comprises the sample chamber and the reference chamber, a ratio of the substantially dry gas and the at least partially saturated gas in the mixture being based on a target humidity; and controlling access to the sample chamber and the reference chamber by controlling movement of the humidity-controlled chamber.

17. A method according to claim 16, further comprising: measuring a temperature within the humidity-controlled chamber; and adjusting the ratio of the substantially dry gas and the at least partially saturated gas in the mixture based on the measured temperature of the humidity-controlled chamber.

18. A method according to claim 16, further comprising: measuring a humidity within the humidity-controlled chamber; and adjusting the ratio of the substantially dry gas and the at least partially saturated gas in the mixture based on a difference between the target humidity and the measured humidity of the humidity-controlled chamber.

19. A method according to claim 16, further comprising: maintaining the temperature of the sample chamber and the reference chamber at substantially a target temperature.

20. A method according to claim 16, wherein the substantially dry gas has a relative humidity of less than about 5%.

21. A method according to claim 20, wherein the substantially dry gas has a relative humidity of less than about 1%.

22. A method according to claim 21, wherein the substantially dry gas has a relative humidity of less than about 0.1%.

23. A method according to claim 16, wherein the at least partially saturated gas has a relative humidity of greater than about 10%.

24. A method according to claim 23, wherein the at least partially saturated gas is a substantially saturated gas having a relative humidity of greater than about 95%.

25. A method according to claim 24, wherein the substantially saturated gas has a relative humidity of greater than about 99%.

26. A method for controlling an atmosphere within a humidity-controlled chamber in a thermogravimetric instrument, the humidity controlled chamber comprising a sample chamber and a reference chamber, the method comprising:
    measuring a temperature within the humidity-controlled chamber;
    flowing a mixture of a substantially dry gas and a substantially saturated gas to the humidity-controlled chamber, a ratio of the substantially dry gas and the substantially saturated gas in the mixture being based on a target humidity and the measured temperature within the humidity controlled chamber; and
    controlling access to the sample chamber and the reference chamber by controlling movement of the humidity-controlled chamber.

27. A method according to claim 26, wherein the substantially dry gas has a relative humidity of less than about 1%.

28. A method according to claim 27, wherein the substantially dry gas has a relative humidity of less than about 0.1%.

29. A method according to claim 26, wherein the substantially saturated gas has a relative humidity of greater than about 99%.

30. A method according to claim 26, further comprising: maintaining the temperature of the sample chamber and the reference chamber at substantially a target temperature.

31. The method of claim 26, wherein the thermogravimetric instrument is configured to calculate a theoretical increase in mass of the at least partially saturated gas based upon an increase in temperature, and configured to adjust the flow of the substantially dry gas and the at least partially saturated gas based upon the calculated theoretical increase in mass.

32. The method of claim 31, wherein the at least partially saturated gas is obtained by exposing a first substantially dry gas to a volatile material, wherein the theoretical increase in mass of the at least partially saturated gas is based upon one or more of the specific first substantially dry gas and the specific volatile material being used.

33. The method of claim 32, wherein the thermogravimetric instrument is configured to perform at least one of a) executing a program according to at least one of the first substantially dry gas and the volatile material and b) performing a look up in a look-up table corresponding to least one of the first substantially dry gas and the volatile material.

34. A humidity-controlled system for a thermogravimetric instrument comprising: a humidity-controlled chamber comprising a sample chamber and a reference chamber; means for controlling a flow of a substantially dry gas and a flow of an at least partially saturated gas to the sample chamber and the reference chamber based on a target humidity; and means for controlling access to the sample chamber and the reference chamber.

35. A humidity-controlled system according to claim 34, wherein said means for controlling access comprises means for controlling movement of the humidity-controlled chamber.

36. A humidity-controlled system according to claim 35, wherein said means for controlling movement comprises an electronic control unit and an actuator, wherein said electronic control unit is configured to control movement of the humidity-controlled chamber with the actuator.

37. A humidity-controlled system according to claim 34, wherein said means for controlling the flow of the substantially dry gas and the flow of the at least partially saturated gas comprises an electronic control unit configured to control (1) a first mass flow controller that generates the flow of the substantially dry gas and (2) a second mass flow controller that generates the flow of the at least partially saturated gas.

38. A humidity-controlled system according to claim 37, wherein the electronic control unit is configured to calculate a ratio of the flow of the substantially dry gas to the flow of the at least partially saturated gas based on the target humidity.

* * * * *